(12) United States Patent
Romano et al.

(10) Patent No.: US 8,652,073 B2
(45) Date of Patent: Feb. 18, 2014

(54) PARAMETERS FOR AN ULTRASOUND DEVICE COMPRISING MEANS TO GENERATE HIGH INTENSITY ULTRASOUND BEAM

(75) Inventors: Fabrizio Romano, Rillieux-la-Pape (FR); Cyril Lafon, Lyon Cedex (FR); Jean-Yves Chapelon, Lyon Cedex (FR); Françoise Chavrier, Lyon Cedex (FR); Alain Birer, Lyon Cedex (FR); Laurent Farcy, Lyon Cedex (FR); Philippe Chapuis, Lyon Cedex (FR)

(73) Assignee: Eye Tech Care, Rillieux-La-Pape (FR)

( * ) Notice: Subject to any disclaimer, the term of this patent is extended or adjusted under 35 U.S.C. 154(b) by 21 days.

(21) Appl. No.: 13/389,044

(22) PCT Filed: Aug. 18, 2009

(86) PCT No.: PCT/EP2009/060682
§ 371 (c)(1),
(2), (4) Date: Feb. 6, 2012

(87) PCT Pub. No.: WO2011/020495
PCT Pub. Date: Feb. 24, 2011

(65) Prior Publication Data
US 2012/0136281 A1 May 31, 2012

(51) Int. Cl.
*A61H 1/00* (2006.01)
(52) U.S. Cl.
USPC .......................................................... 601/2
(58) Field of Classification Search
USPC .......................................................... 601/2
See application file for complete search history.

(56) References Cited

U.S. PATENT DOCUMENTS

| 4,484,569 A | 11/1984 | Driller et al. |
| 2002/0055736 A1* | 5/2002 | Horn et al. ........................ 606/26 |
| 2008/0275370 A1* | 11/2008 | McIntyre et al. ................. 601/2 |

FOREIGN PATENT DOCUMENTS

| DE | 44 30 720 | 6/1995 |
| WO | 02/45073 | 6/2002 |
| WO | 2006/136912 | 12/2006 |
| WO | 2009/103721 | 8/2009 |

OTHER PUBLICATIONS

Mueller; Biomed Tech (Berl).; Apr. 1989; vol. 34; No. 4; pp. 62-72.
International Search Report Based on PCT/EP2009/060682 Mailed Oct. 6, 2010.
Coleman et al.; "Therapeutic Ultrasound"; 1986; Ultradsound in Med. & Biol.; vol. 12; No. 8; pp. 633-638.

\* cited by examiner

*Primary Examiner* — Tse Chen
*Assistant Examiner* — Hien Nguyen
(74) *Attorney, Agent, or Firm* — Miles & Stockbridge, PC

(57) ABSTRACT

The present invention relates to a device for treatment of an ocular pathology, the device comprising at least one eye ring wherein the proximal end of said eye ring is suitable to be applied onto the globe and means to generate ultrasound beam fixed on the distal end of the eye ring, said means to generate ultrasound beam presenting a concave segment shape conformed along a single curvature corresponding to a single direction wherein the concavity is designed to be tuned towards the eyeglobe.

15 Claims, 2 Drawing Sheets

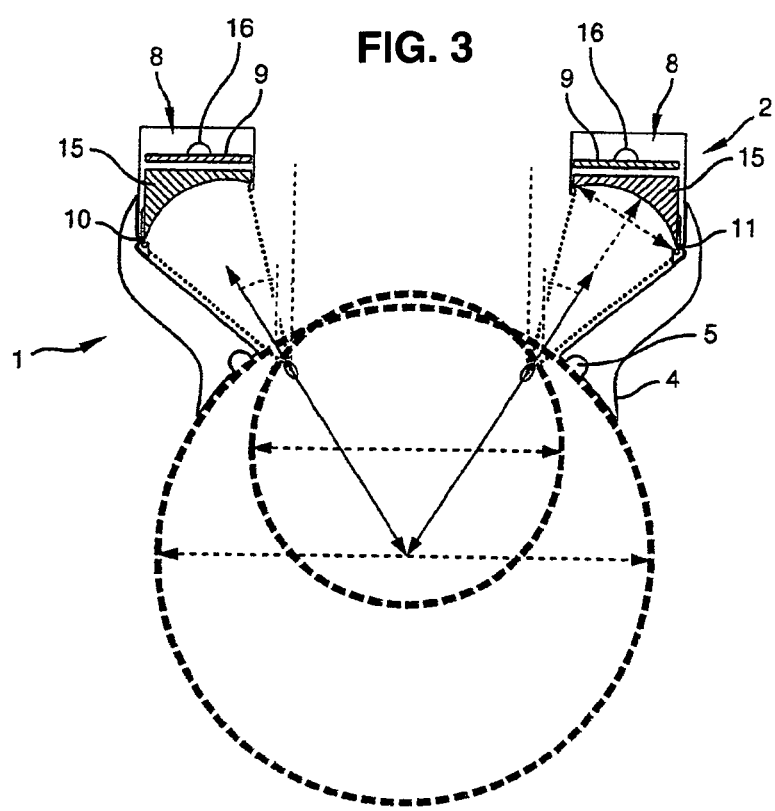

PARAMETERS FOR AN ULTRASOUND DEVICE COMPRISING MEANS TO GENERATE HIGH INTENSITY ULTRASOUND BEAM

CROSS REFERENCE TO RELATED APPLICATIONS

This application is a §371 National Stage Application of PCT/EP2009/060682, filed Aug. 18, 2009.

BACKGROUND OF THE INVENTION

1. Field of the Invention

The present invention is generally directed to a non invasive treatment for ocular pathology, and relates more particularly to a device and method for generating high intensity focused ultrasound onto at least one annular segment of the ciliary body of an eye affected by glaucoma.

2. Description of Related Art

In the field of ophthalmologic disease, it is well known that glaucoma is a significant public health problem, between 1 to 2% of population being suffering from this pathology, because glaucoma is a major cause of blindness.

The World health organisation considers glaucoma as the third cause of blindness in the world, responsible of 15% of declared blindness occurrences, with an incidence of 2.4 millions persons per year.

The evolution of glaucoma is slow. Glaucoma is an insidious health disease because at the first stage glaucoma is asymptomatic; the patient does not feel any pain or any visual problem. When the first visual troubles appear, lesions are commonly already large and despite irreversible.

The blindness that results from glaucoma involves both central and peripheral vision and has a major impact on an individual's ability to lead an independent life.

Glaucoma is an optic neuropathy, i.e. a disorder of the optic nerve, which usually occurs in the setting of an elevated intraocular pressure. The pressure within the eye increases and this is associated with changes in the appearance and function of the optic nerve. If the pressure remains high enough for a long enough period of time, total vision loss occurs. High pressure develops in an eye because of an internal fluid imbalance.

The eye is a hollow structure that contains a clear fluid called "aqueous humor." Aqueous humor is formed in the posterior chamber of the eye by the ciliary body. The fluid, which is made at a fairly constant rate, then passes around the lens, through the pupillary opening in the iris and into the anterior chamber of the eye. Once in the anterior chamber, the fluid drains out of the eye through two different routes. In the "uveoscleral" route, the fluid percolates between muscle fibers of the ciliary body. This route accounts for approximately ten percent of the aqueous outflow in humans. The primary pathway for aqueous outflow in humans is through the "canalicular" route that involves the trabecular meshwork and Schlemm's canal.

With the increased pressure in the eye, the aqueous fluid builds up because it cannot exit fast enough. As the fluid builds up, the intraocular pressure (IOP) within the eye increases. The increased IOP compresses the axons in the optic nerve and also may compromise the vascular supply to the optic nerve. The optic nerve carries vision from the eye to the brain. Some optic nerves seem more susceptible to abnormally elevated IOP than other eyes.

The only therapeutic approach currently available in glaucoma is to reduce the intraocular pressure.

The clinical treatment of glaucoma is approached in a step-wise fashion. Medication often is the first treatment option except for congenital glaucoma wherein surgery is the primary therapy.

Administered either topically or orally, these medications work to either reduce aqueous production or they act to increase outflow. Currently available medications may have many serious side effects including: congestive heart failure, respiratory distress, hypertension, depression, renal stones, aplastic anemia, sexual dysfunction and death.

The commonly used medications are Prostaglandin or analogs like latanoprost (Xalatan), bimatoprost (Lumigan) and travoprost (Travatan) which increase uveoscleral outflow of aqueous humor; Topical beta-adrenergic receptor antagonists such as timolol, levobunolol (Betagan), and betaxolol which decrease aqueous humor production by the ciliary body; Alpha2-adrenergic agonists such as brimonidine (Alphagan) which work by a dual mechanism, decreasing aqueous production and increasing uveo-scleral outflow; Less-selective sympathomimetics like epinephrine and dipivefrin (Propine) which increase outflow of aqueous humor through trabecular meshwork and possibly through uveoscleral outflow pathway; Miotic agents (parasympathomimetics) like pilocarpine which work by contraction of the ciliary muscle, tightening the trabecular meshwork and allowing increased outflow of the aqueous humour; Carbonic anhydrase inhibitors like dorzolamide (Trusopt), brinzolamide (Azopt), acetazolamide (Diamox) which provide a reduction of aqueous humor production by inhibiting carbonic anhydrase in the ciliary body. The two most prescribed medications are currently topical Prostaglandin Analogs and Betablockers.

Compliance with medication is a major problem, with estimates that over half of glaucoma patients do not follow their correct dosing schedules. Fixed combinations are also prescribed extensively since they improve compliance by simplifying the medical treatment.

When medication fails to adequately reduce the pressure, often surgical treatment is performed as a next step in glaucoma treatment. Both laser and conventional surgeries are performed to treat glaucoma. Generally, these operations are a temporary solution, as there is not yet a cure which is completely satisfactory for glaucoma.

There are two different approaches to treat glaucoma: either the surgeon tries to improve aqueous humor drainage, or he tries to reduce its production.

The most practiced surgeries intended to improve the aqueous humor drainage are: canaloplasty, laser trabeculoplasty, laser peripheral iridotomy (in case of angle closure glaucoma), trabeculectomy, deep non perforating sclerectomy and glaucoma drainage implants.

The most practiced surgery intended to reduce aqueous humor production is the cyclodestruction technique. When cyclodestruction is performed with a laser, it is called cyclophotocoagulation. High Intensity Focused Ultrasound can be used to obtain a cyclodestruction.

It has been imagined using controlled ultrasonic energy in the treatment of glaucoma. "Therapeutic ultrasound in the treatment of glaucoma. I. Experimental model—Coleman D J, Lizzi F L, Driller J, Rosado A L, Chang S, Iwamoto T, Rosenthal D—PMID: 3991121 (PubMed) 1985 March; 92(3): 339-46" discloses a treatment of glaucoma applying High Intensity Focused Ultrasound (HIFU) onto the ciliary body to provide filtration and focal disruption of ciliary epithelium treating elevated intraocular pressure in a non invasive manner.

An apparatus associated to this treatment using controlled ultrasonic energy in the treatment of glaucoma is also described in U.S. Pat. No. 4,484,569.

However, such apparatus which was manufactured and distributed under the commercial name of SONOCARE was very difficult to manipulate. Moreover such apparatus allows to treat only one punctual zone at a time.

Thus each shot needs to be repeated many time to treat all the circumference of the eye and all the apparatus needs to be handled, placed and calibrated many times, thus taking a very long time (i.e. displacement of the ultrasonic means, verification of the position of the ultrasonic means with regard to the punctual region to be treated with optical and echographic sighting means, filling of the device with coupling liquid and production of a ultrasonic shot).

Moreover, tissues at the neighbourhood of the treatment area can be destroyed leading to blurred vision, eye muscle imbalance or double vision.

SUMMARY OF THE INVENTION

There is a need for an accurate, safe, effective and inexpensive method of treating an ocular pathology by applying easily and safely high intensity focused ultrasound onto the eye to be treated and for a device thereof.

The above-mentioned need is addressed by the embodiments described herein in the following description of the invention which allows unlike other HIFU treatments to treat the eye which is more safety for tissues at the neighbourhood of the treatment area.

Another aim of the present invention is to provide a method and a device which allows treating the whole circumference of the eye in only one step, without the necessity to manipulate the device during the procedure.

In one embodiment, a device for treatment of an ocular pathology is disclosed.

Said device comprises means to generate high intensity focused ultrasound beam onto the eye, and a control unit connected to the means to generate high intensity focused ultrasound beam. Advantageously, the control unit controls the duration and the frequency of the high intensity focused ultrasound beam generated by said means, the duration being in a range of about 3 to 6 seconds, and more preferably equal to about 3 seconds, and the frequency being in a range of about 19 to 23 MHz, and more preferably equal to about 21 MHz.

BRIEF DESCRIPTION OF THE DRAWINGS

FIG. 3 is an elevation view of the device during the generation of HIFU energy.

DETAILED DESCRIPTION OF A PREFERRED EMBODIMENT

Figure 1:
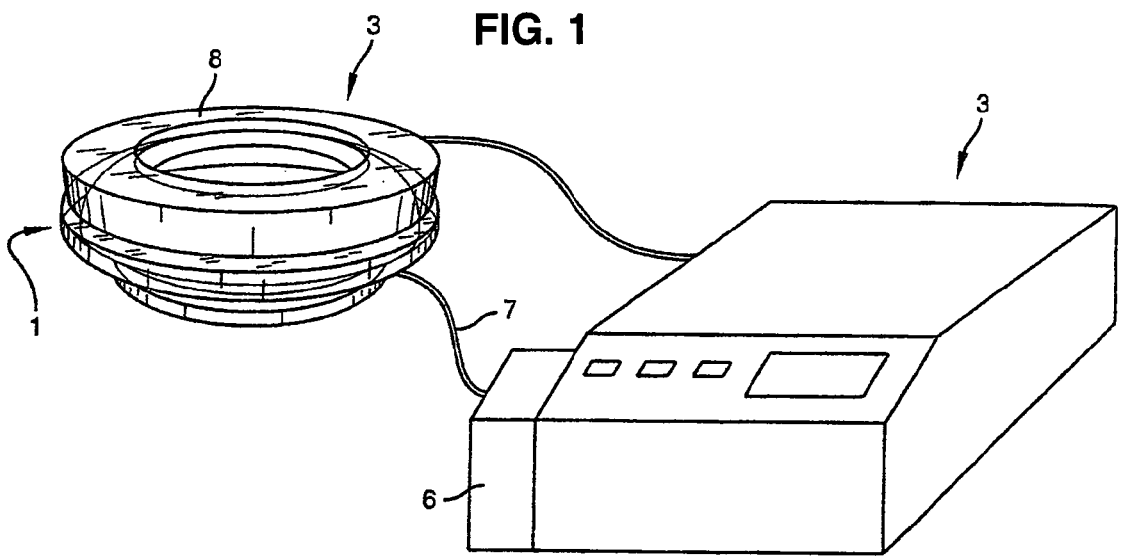
FIG. 1 is a schematic perspective view of the device for treatment of an ocular pathology by applying high intensity focused ultrasound according to the invention.

Preferably, the control unit further controls the power of the high intensity focused ultrasound beam generated by said means, said power being in a range of about to 1 acoustic Watt to 5 acoustic Watt, and more preferably equal to about 2 acoustic Watt.

In a preferred embodiment, the device further comprises at least one eye ring wherein the proximal end of said eye ring is suitable to be applied onto the globe, the means being adapted to be applied on the distal end of the eye ring.

In a variant of the present invention, the means to generate high intensity focused ultrasound beam comprise at least two piezoelectric elements, and preferably six piezoelectric elements. The piezoelectric element can be made of piezo-composite or piezo-ceramic material.

Preferably, the piezoelectric elements are activated sequentially by the control unit. This allows limiting heat accumulation in the center of the device. The surface of each cylindrical piezoelectric element is preferably of about 30 $mm^2$ with a curvature radius of about 10.2 mm. At a frequency of 21 MHz, the focal gain G, is of about 60, as the −6 dB isocontour around the focal line has a surface of about 0.5 $mm^2$ compared to the 30 mm2 of surface of the transducer. For a sound power of about 2 acoustic Watts, this corresponds to an instantaneous acoustic intensity (i.e. quotient of the instantaneous acoustic power transmitted across a surface element and the area of the surface element) of about 6.65 $W/cm^2$, and a sound intensity at the focal point of about $6.5 \times G = 390$ $W/cm^2$, and thus to a dose of 1170 Joules/$cm^2$ for a shot having a duration of 3 seconds.

In another embodiment, a method of treating an ocular pathology by generating high intensity focused ultrasound onto at least one eye's area is disclosed.

The method comprises at least the following steps of:
generating high intensity focused ultrasound energy onto the eye,
controlling the generation of the high intensity focused ultrasound beam.

The controlling step comprises controlling the duration and the frequency of the high intensity focused ultrasound beam, the duration being in a range of about 3 to 6 seconds, and more preferably equal to about 3 seconds, and the frequency being in a range of about 19 to 23 MHz, and more preferably equal to about 21 MHz.

Advantageously, the controlling step can further comprise controlling the power of the high intensity focused ultrasound beam, said power being in a range of about to 1 acoustic Watt to 5 acoustic Watt, and preferably equal to about 2 acoustic Watt.

In one embodiment, the method further comprises positioning at least one eye ring wherein the proximal end of said eye ring is suitable to be applied onto the globe, and applying the means on the distal end of the eye ring.

Embodiments of varying scope are described herein. In addition to the aspects described in this summary, further aspects will become apparent by reference to the drawings and with reference to the detailed description that follows.

Figure 2:
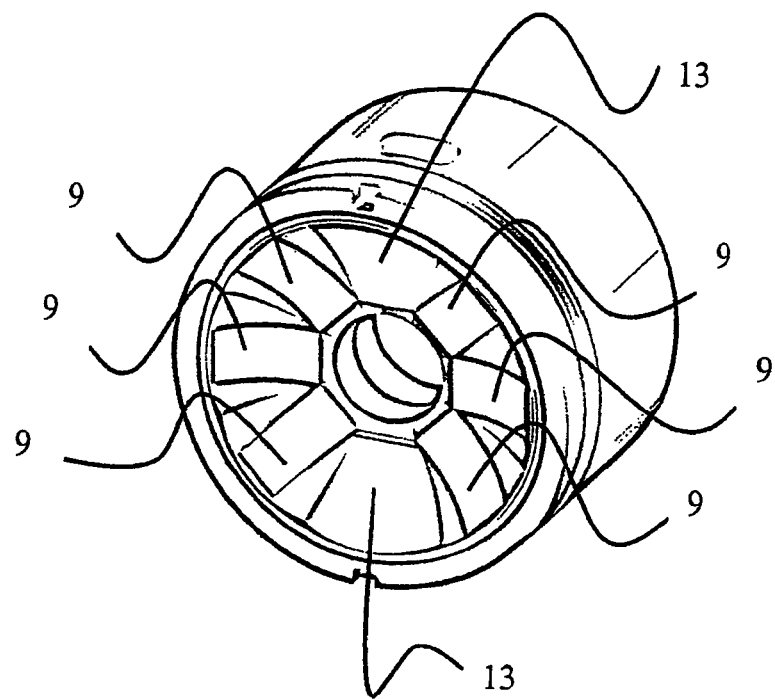
FIG. 2 is a perspective view of the a portion of the device illustrated on FIG. 1.

FIG. 1 is a schematic perspective view of the device for treatment of an ocular pathology by applying high intensity focused ultrasound according to the invention, FIG. 2 is a perspective view of the a portion of the device illustrated on FIG. 1, FIG. 3 is an elevation view of the device during the generation of HIFU energy, We will disclose hereinafter a method and a device suitable for the treatment of glaucoma; nevertheless, it is obvious that the skilled person could adapt the method and the device for the treatment of any ophthalmologic pathology that necessitate surgery without departing of the scope of the invention.

The device according to the invention is disclosed in the PCT application filed under the number PCT/EP2009/051892 incorporated herein by reference.

Referring to FIG. 1 to 3, the device according to the invention comprises an eye ring 1 wherein the proximal end of said eye ring is suitable to be applied onto the globe of the eye to be treated and means 2 to generate high intensity focused ultrasound energy, said means being fixed on the distal end of the eye ring.

Said means 2 fixed on the distal end of the eye ring are suitable to generate high intensity focused ultrasound beam. According to another embodiment of the invention, said means fixed on the distal end of the eye ring are suitable to generate scattered ultrasound beam.

Said means 2 are connected to a control unit 3 including a burst generator and means specifying the parameters of the burst such as the frequency, the power and the duration of each burst, the number of bursts (i.e. the number of transducers to be activated), etc. . . . . . The burst generator comprises at least a sine-wave signal generator at a determined frequency comprised between 19 and 23 MHz, and preferably equal to about 21 MHz, an amplifier and a Power meter.

The penetration level of ultrasound beam depends on the frequency of said ultrasound beam. In particular, low frequency ultrasound beam penetrates more deeply than high frequency ultrasound beam.

The inventors have determined that if the frequency of the ultrasound beam is lower than 19 MHz, there is a risk that the beam penetrates to deeply so that tissues at the neighbourhood of the ciliary body may be damaged by the ultrasound beam.

The inventors also determined that if the frequency of the ultrasound beam is higher than 23 MHz, there is a risk that the ultrasound beam does not penetrate enough into the eye so that the ultrasound beam does not destroy the ciliary body.

Consequently, considering that the target for the ultrasound beam, i.e. the ciliary body are positioned 2 mm under the eye globe surface, an ultrasound beam having a frequency in a range of about 19 MHz to 23 MHz is preferred.

Furthermore, the risks associated to the treatment are time dependent. The longer the operative time is, the greater the risk is.

Indeed, the eye of the patient can move during the operation, etc.

The duration of the energy generated by the means 2 is preferably in a range of about 3 second to 6 seconds, and more preferably equal to about 3 seconds.

This very short duration allows minimizing the risk of error due to the operative time and increase the comfort for the patient and the practitioner during the treatment.

Preferably, control unit (3) further controls the power of the high intensity focused ultrasound beam generated by said means 2.

The power of the high intensity ultrasound beam is in a range of about to 1 acoustic Watt to 5 acoustic Watt, and more preferably equal to about 2 acoustic Watt.

The eye ring 1 consists in a sawn-off cone element open at both ends wherein the small base is the proximal end and the large base is the distal end.

The proximal end of the sawn-off cone element 1 comprises an external annular flange 4 suitable to be applied onto the eye globe.

The proximal edge of the sawn-off cone element comprises an annular groove 5 communicating with at least one hose 7 formed in the sawn-off cone element 1 and connected to a suction device.

The internal diameter of the proximal end of the sawn-off cone element 1 is sensibly equal to the corneal diameter plus 2 to 6 mm, and more preferably equal to the sum of the corneal diameter with a value of 4 millimeters.

The internal diameter of the proximal end of the sawn-off cone element 1, depending on the patient corneal diameter, can be comprised between 12 and 18 mm and the internal diameter of the distal end of the sawn-off cone element 1 can be comprised between 26 and 34 mm.

Moreover, the height of the sawn-off cone element 1 is comprised between 8 and 12 mm.

The sawn-off cone element 1 is in medical grade polymer.

The means 2 to generate high intensity focused ultrasound energy consists in at least two transducers 9 and more preferably six transducers 9, fixed on the distal end of the sawn-off cone element 1 in such a way that said transducers 9 extend toward the revolution axis of said sawn-off cone element 1.

Said transducers 9 can be made either in piezocomposite material or in piezoceramic material or in other materials which complies with the production of High Intensity Ultrasound. Said transducers 9 can be focused by themselves and have a toric geometry, or a cylindrical geometry or a spherical geometry, or an elliptical geometry or they can be flat and be used in combination with a focusing system like acoustic lens or acoustic reflectors 15, with a variety of shapes and materials, extending under or in front of said flat annular transducers.

Acoustic reflectors 15 are well known in therapeutic ultrasound and are currently routinely used in external shockwave lithotripsy (Focusing water shock waves for lithotripsy by various ellipsoid reflectors—Müller M.—Biomed Tech (Berl). 1989 April; 34(4):62-72).

According to another embodiment of the invention, said means 2 to generate high intensity dynamically focused ultrasound energy consists in at least two flat transducers 9 having a cylindrical segment shape, fixed on the distal end of the sawn-off cone element 1 in such a way that said transducers 9 extend toward the revolution axis of said sawn-off cone element 1.

Alternatively, said means 2 to generate scattered ultrasound beam are means to generate high intensity non focused ultrasound energy consisting in at least two transducers 9 having an annular flat segment shape, fixed on the distal end of the sawn-off cone element 1 in such a way that said transducers 9 extend toward the revolution axis of said sawn-off cone element 1.

Moreover, said transducers 9 are connected to the control unit 3.

Said device comprises two pairs of three transducers 9 separated by two inactive sectors 13.

Transducers 9 are successively activated by the control unit 3 or simultaneously activated by said control unit 3.

One advantage of the device according to the present invention is that the means 2 to generate ultrasound beam fixed on the distal end of the eye ring 1 comprise a plurality of transducers arranged according to a treatment pattern.

This allows treating the eye circumferentially in one time. Indeed, unlike the methods and apparatuses described for instance in U.S. Pat. No. 4,484,569 and in DE 44 30 720, the apparatus according to the invention allows treating the eye without the need to repeat an operation many times.

With regard to U.S. Pat. No. 4,484,569 and DE 44 30 720, the invention allows in particular:

simplifying the operation procedure by providing a device which allows a treatment of the eye in one time; indeed, once the apparatus is placed and fixed onto the eye, the apparatus stay in position and the treatment of the whole circumference of the eye can be realized without the need for the operator to displace or maintain the apparatus, providing a reproducible procedure; indeed unlike the apparatus of the prior art, the device of the present invention do not need to be displaced many times to treat different punctual zones of the region to be treated, generating extended lesions covering large regions of the ciliary body unlike the apparatus of the prior art which generates only punctual lesions and needs many elementary lesions to be effective, reducing the operative time which reduces the error risk factor and thus improve the quality of the treatment, providing a treatment which is less dependent from the operator, because very easy to be performed, very easy to be learned with an extremely short learning curve, and relatively automatic during the treatment time.

In a preferred embodiment, the invention relates to a device for treatment of an ocular pathology, the device comprising at least one eye ring 1 wherein the proximal end of said eye ring 1 is suitable to be applied onto the globe and means 2 to generate ultrasound beam fixed on the distal end of the eye ring 1, said means 2 to generate ultrasound beam presenting a concave segment shape conformed along a single curvature corresponding to a single direction wherein the concavity is designed to be tuned towards the eyeglobe.

Preferably, the single direction is perpendicular to the revolution axis of the eye ring 1.

The use of means to generate ultrasound beam presenting a concave segment shape conformed along a single curvature corresponding to a single direction instead of means 2 to generate ultrasound beam having a toric geometry allows eliminating the risk of having a plurality (at least two) focalisation regions, simplifying the manufacturing process making it possible to manufacture various diameters of the means to generate ultrasound beam without changing tools, obtaining a lesion shape which is almost identical to that obtained with toric elements.

In one embodiment of the present invention, the means 2 to generate high intensity focused ultrasound energy comprise a standing crown 8 holding at least two transducers 9 having a concave segment shape conformed along the single curvature corresponding to the single direction, said standing crown 8 being fixed on the distal end of the eye ring 1 in such a way that the transducers 9 extend toward the revolution axis of said eye ring.

In another embodiment, the means 2 to generate high intensity focused ultrasound energy comprise a standing crown 8 holding at least two transducers and a at least two focusing acoustic elements 15 extending under a respective transducer 9, each focusing acoustic element 15 having a concave segment shape conformed along the single curvature corresponding to the single direction, said standing crown 8 being fixed on the distal end of the eye ring 1 in such a way that the focusing acoustic element 15 extend toward the revolution axis of said eye ring 1. Each transducer 9 can be a flat segment having a globally rectangular profile that extends sensibly parallel to the proximal and distal edge of the eye ring.

Advantageously, the concave segment shape can be a cylindrical segment shape or an elliptical segment shape.

Preferably, the transducers 9 are arranged according to a treatment pattern.

It will be understood in the case of the present invention that the treatment pattern corresponds to the form defined by the regions to be treated. In the case of the treatment of the ciliary bodies, the treatment pattern may be annular or semi-annular. In other cases, the treatment pattern may be elliptical, or hexagonal or octagonal.

For instance, in one embodiment, the transducers 9 can be placed peripherally over the standing crown according to the treatment pattern. More preferably, the transducers 9 are placed peripherally over the whole or a part of the standing crown. In particular, the transducers 9 can be placed circumferentially over the whole or a part of the circumference of the standing crown.

The method of treating an annular pathology according to the invention will now be described in more details.

In a first step, the user positions the eye ring 1 onto the eye to be treated. Then the user positions the means 2 to generate the high intensity ultrasound beam onto the distal end of the eye ring 1.

In a second step, the user activate said means 2 so that a high intensity ultrasound beam is generated at a frequency between 19 and 23 MHz during a period comprised in a range of about 3 to 6 seconds.

In one embodiment, the frequency and the duration of the high intensity ultrasound beam are adjusted by the user using input means. In another embodiment the frequency and the duration of the high intensity ultrasound beam are preset in the control unit 3. The user only activates the generation of the high intensity ultrasound beam, for instance by pushing a button, and the control unit 3 controls the frequency and the duration of the high intensity ultrasound beam.

This written description uses examples to disclose the invention, including the best mode, and also to enable any person skilled in the art to make and use the invention. The scope of the subject matter described herein is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A device for treating glaucoma comprising:
a generator is configured to generate high intensity focused ultrasound beam onto at least one annular segment of a ciliary body of an eye affected by glaucoma,
a control unit connected to the generator, wherein said control unit is configured to controls duration and frequency of the high intensity focused ultrasound beam generated by said generator, the duration being in a range of about 3 to about 6 seconds and the frequency being in a range of about 19 to about 23 MHz specific to only glaucoma treatment,
wherein the device is configured to only treat glaucoma and treat the whole circumference of the eye in only one step.

2. The device according to claim 1, wherein said control unit is configured to control power of the high intensity focused ultrasound beam generated by said generator, said power being in a range of from about 1 acoustic Watt to about 5 acoustic Watt.

3. The device according to claim 2, wherein said power is about 2 acoustic Watt.

4. The device according to claim 1, wherein said frequency is about 21 MHz.

5. The device according to claim 1, wherein said duration is about 3 seconds.

6. The device according to claim 1, wherein said device comprises at least one eye ring wherein a proximal end of said eye ring is capable of being applied onto a globe, said generator being adapted to be applied on a distal end of said eye ring.

7. The device according to claim 1, wherein said generator comprises at least two piezoelectric elements activated sequentially by said control unit.

8. The device according to claim 7, wherein each said piezoelectric element has a surface of about 30 mm$^2$.

9. A method of treating glaucoma by generating high intensity focused ultrasound onto at least one annular segment of a ciliary body of an eye affected by glaucoma, the method comprising at least the following:

generating high intensity focused ultrasound energy onto said annular segment of a ciliary body of an eye affected by glaucoma, controlling said generation of the high intensity focused ultrasound beam, wherein said controlling comprises controlling duration and frequency of said high intensity focused ultrasound beam, said duration being in a range of from about 3 to about 6 seconds and said frequency being in a range of from about 19 to about 23 MHz, wherein the method treats the whole circumference of the eye in only one step.

10. The method according to claim 9, wherein said controlling comprises controlling power of said high intensity focused ultrasound beam, said power being in a range of from about 1 acoustic Watt to 5 about acoustic Watt.

11. The method according to claim 10, wherein said power is about 2 acoustic Watt.

12. The method according to claim 9, wherein said frequency is about 21 MHz.

13. The method according to claim 9, wherein said duration is about 3 seconds.

14. The method according to claim 9, comprising positioning at least one eye ring wherein a proximal end of said eye ring is suitable to be applied onto a globe, and applying a generator on a distal end of said eye ring.

15. The device according to claim 1, wherein the generator comprises a plurality of transducers arranged according to a treatment pattern.

* * * * *

UNITED STATES PATENT AND TRADEMARK OFFICE
CERTIFICATE OF CORRECTION

| | | |
|---|---|---|
| PATENT NO. | : 8,652,073 B2 | Page 1 of 1 |
| APPLICATION NO. | : 13/389044 | |
| DATED | : February 18, 2014 | |
| INVENTOR(S) | : Fabrizio Romano et al. | |

It is certified that error appears in the above-identified patent and that said Letters Patent is hereby corrected as shown below:

On the Title Page

Item (75) address of inventor Laurent Farcy should be changed from "Lyon Cedex" to --Liergues--.

Item (75) address of inventor Philippe Chapuis should be changed from "Lyon Cedex" to --Pommiers--.

Signed and Sealed this
Thirty-first Day of March, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,652,073 B2 | Page 1 of 1 |
| APPLICATION NO. | : 13/389044 | |
| DATED | : February 18, 2014 | |
| INVENTOR(S) | : Fabrizio Romano et al. | |

It is certified that error appears in the above-identified patent and that said Letters Patent is hereby corrected as shown below:

ON THE TITLE PAGE

The (73) Assignees should be changed from "Eye Tech Care, Rillieux-La-Pape (FR)" to --Eye Tech Care, Rillieux-La-Pape (FR) and Institut National de la Sante et de la Recherche Medicale (INSERM), Paris (FR)--.

Signed and Sealed this
Thirteenth Day of October, 2015

Michelle K. Lee
*Director of the United States Patent and Trademark Office*